United States Patent [19]

Takayama

[11] 4,349,255

[45] Sep. 14, 1982

[54] PHOTOGRAPHING APPARATUS FOR AN ENDOSCOPE

[75] Inventor: Syuichi Takayama, Hachioji, Japan

[73] Assignee: Olympus Optical Co., Ltd., Tokyo, Japan

[21] Appl. No.: 242,635

[22] Filed: Mar. 11, 1981

[30] Foreign Application Priority Data

Mar. 14, 1980 [JP] Japan ................... 55-32361

[51] Int. Cl.³ ................................. G03B 7/08
[52] U.S. Cl. ........................ 354/31; 354/33; 354/62
[58] Field of Search ............... 354/31, 62, 33

[56] References Cited

U.S. PATENT DOCUMENTS

| | | |
|---|---|---|
| 3,440,938 | 4/1969 | Stimson et al. .............. 354/31 |
| 3,591,829 | 7/1971 | Murata et al. .............. 354/31 |
| 3,599,630 | 8/1971 | Sato et al. |
| 3,670,722 | 6/1972 | Kosaka |
| 3,683,766 | 8/1972 | Nobusawa |
| 3,836,924 | 9/1974 | Kawasaki |
| 3,906,516 | 9/1975 | Harvey .............. 354/31 |
| 4,153,356 | 5/1979 | Hama |

*Primary Examiner*—Russell E. Adams
*Attorney, Agent, or Firm*—Frishauf, Holtz, Goodman and Woodward

[57] ABSTRACT

A photographing apparatus for an endoscope comprises a first photodetector for detecting part of the light projected from an image guide of an endoscope and a second photodetector for detecting part of the flash light guided in a light guide of the endoscope. A resistor is connected in parallel with the first photodetector. A voltage induced across the two ends of the resistor is amplified and is supplied to an integrating circuit until the voltage is saturated. When the voltage induced across the two ends of the resistor is saturated, a voltage induced in the second photodetector is supplied to the integrating circuit after amplification and level adjustment. When the output from the integrating circuit reaches a predetermined level, supply of the flashlight to the light guide is interrupted.

5 Claims, 8 Drawing Figures

PHOTOGRAPHING APPARATUS FOR AN ENDOSCOPE

BACKGROUND OF THE INVENTION

The present invention relates to a photographing apparatus for an endoscope and, more particularly, to an automatic exposure controller such for a photographing apparatus.

In a photographing apparatus for an endoscope comprising a camera unit and a light source unit mounted to the endoscope, a photosensitive element or photodetector is disposed inside the eyepiece part of the endoscope or the camera unit for measuring the luminosity of light incident on the film inside the camera unit. According to the photoelectric signal from the photosensitive element, the automatic exposure control unit of the photographing apparatus calculates the luminosity of the light incident on the film. When this calculated amount of light reaches the proper exposure value, supply of the photographing light emitted from the light source unit is interrupted and the film is exposed to the optimal amount of light.

The photosensitive element has photoelectric conversion characteristics perculiar to itself; therefore the precise amount of light incident on the film may not be measured by the photocurrent generated by the photosensitive element directly as an object luminance signal corresponding to the light intensity of the film surface. This is because the commercially available photosensitive elements do not uniformly generate photoelectric signals of the same level for an object of a given luminosity. In order to solve these problems, a conventional photographing apparatus for an endoscope has been proposed in which a resistor for adjusting sensitivity is connected in parallel with the photosensitive element, and the resistance of this resistor is suitably adjusted so that the variations in the photoelectric conversion characteristics of the photosensitive element may be compensated and the correct luminosity information may be obtained. When light of a certain luminosity is projected on the photosensitive element, the resistance of the sensitivity-adjusting resistor is so adjusted that the proper voltage is induced across the two ends of the sensitivity-adjusting resistor by the photocurrent generated by the photosensitive element, and this voltage may then be supplied to the automatic exposure apparatus as an object luminance signal.

However, as has been described, when the resistor is connected in parallel with the photosensitive element, the amount of light projected on the photosensitive element becomes great. When the voltage generated across the resistor reaches a predetermined level, the current flowing through the photosensitive element is saturated, in which event the voltage of the resistor may no longer correspond directly to the illumination of the film surface, resulting in overexposure.

It is an object of the present invention to provide a photographing apparatus for an endoscope which is capable of constantly providing a proper exposure.

SUMMARY OF THE INVENTION

According to the present invention, there is provided a photographing apparatus for an endoscope comprising:

an endoscope having a light guide for transmitting light to a region to be photographed, and an image guide for transmitting light reflected from the region to be photographed;

a flash light source for emitting light for photographing into the light guide of said endoscope;

a camera unit for housing a film to which is projected a light beam transmitted through the image guide of said endoscope, said camera unit having shutter means disposed on the optical path of the light beam for opening and closing the optical path, and further having means for generating a synchronous signal for opening the shutter means;

a first photoelectric converter for detecting part of the light beam transmitted through said light guide;

a first amplifier for amplifying a voltage generated across a resistor connected in parallel with said first photoelectric converter;

means for generating a switching signal when a first voltage signal amplified by said first amplifier has reached a predetermined level;

a second photoelectric converter for detecting part of the flash of light generated by said flashlight source;

a second amplifier for amplifying a voltage generated by said second photoelectric converter;

means for holding the level of a second voltage signal amplified by said second amplifier in response to said switching signal and for generating a correction signal obtained by amplifying the second voltage signal of this level by a constant factor;

means for generating a divided signal obtained by dividing said second voltage signal generated by said second amplifier by said correction signal;

means for integrating a supplied signal;

switching means for switching the signal supplied to said integrating means from said first voltage signal to said divided signal in response to said switching signal;

means for generating a flash-terminating signal when the output from said integrating means reaches a predetermined level; and means for energizing said flash light source in response to a synchronous signal and for deenergizing said flashlight source in response to said flash-terminating signal.

BRIEF DESCRIPTION OF THE DRAWINGS

FIG. 1 schematically shows an embodiment of an endoscope incorporating a photographing apparatus according to an embodiment of the present invention.

DETAILED DESCRIPTION

Figure 1:
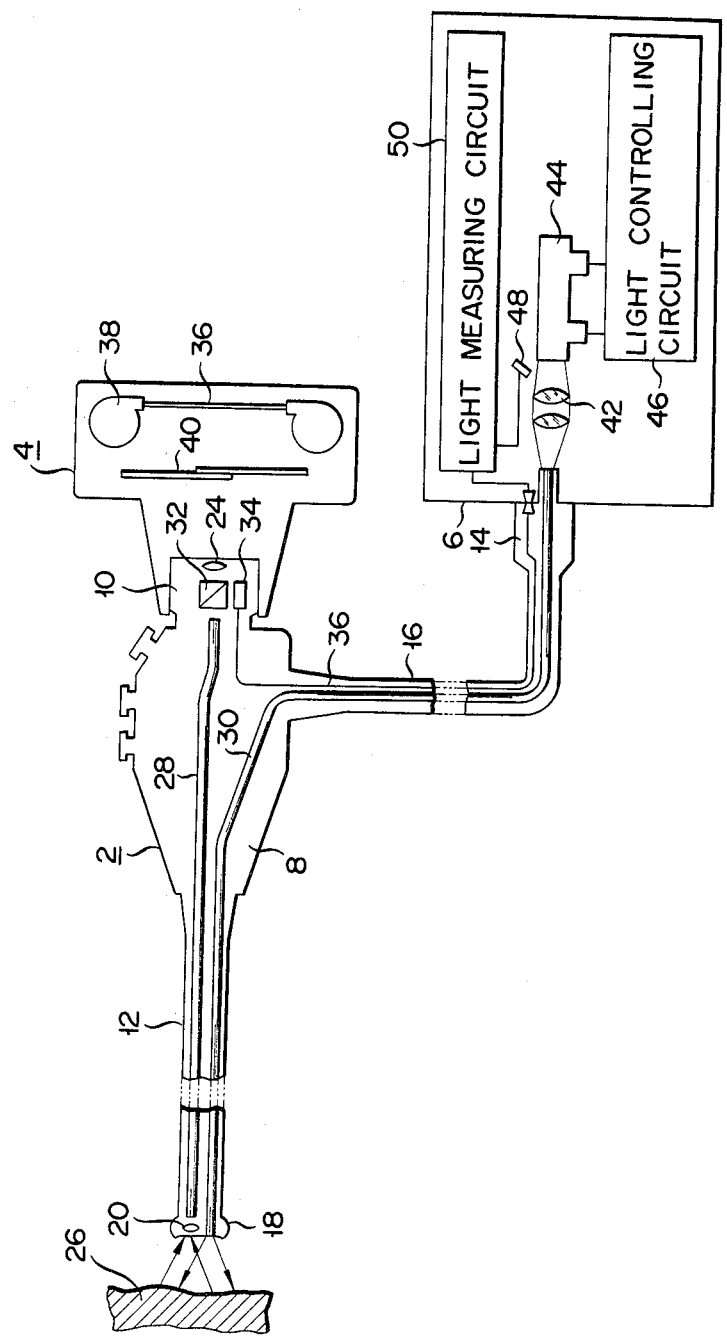
FIG. 1 is a schematic view of a photographing apparatus for an endoscope according to an embodiment of the present invention.

The endoscope system, as is well known, comprises an endoscope 2, a camera unit 4 and a light source unit 6. The endoscope 2 has a control section 8 for controlling endoscope operation. A mount of the camera unit 4 is mounted to an eyepiece part 10 projecting from the control section 8. A universal cord 16, having a connector 14 coupled to the light source unit 6, and an insertion section 12 inserted in the body cavity (not shown), projects from the control section 8. An objective lens 20 is disposed inside a distal end 18 of the insertion section 12, and an eyepiece lens 24 is disposed inside the eyepiece part 10. An image guide 28 for transmitting the image of a to-be-examined region 26 extends between the objective lens 20 and the eyepiece lens 24 through the insertion section 12 and the control section 8. A light guide 30 for transmitting light for photographing or examining to the to-be-examined region 26 extends from the distal end 18 through the insertion section 12, the control section 8, the universal cord 16, and the connector 14 into the light source unit 6. A beam splitter 32 for splitting the light transmitted through the image guide 28 is disposed in the optical path between the image guide 28 and the eyepiece lens 24. In the path of the light reflected by the beam splitter 32 is disposed a first photodetector or a photodetecting element 34 for detecting this reflected light. A signal line 36 for transmitting a detected signal extends from the first photodetector 34 through the universal cord 16 and is connected to the connector pins of the connector 14.

A cartridge 38 for housing film 36 on which is projected an image of the region 26 from the eyepiece lens 24 is mounted inside the camera unit 4. A focal plane shutter 40 is interposed between the film 36 and the eyepiece 24.

Inside the light source unit 6 are disposed a condenser lens 42 for guiding the light to the end face of the light guide 30 and an electric flash lamp 44 for emitting light to the light guide 30 through the condenser lens 42. A light controlling circuit 46 for controlling the electric flash lamp 44 is connected to this lamp 44. A second photodetector or photosensitive element 48 for detecting the flash light generated by the electric flash lamp 44 is disposed inside the light source unit 6. A light measuring circuit 50 to which the luminance signals are supplied from the first and second photodetectors 34 and 48 and which generates a flash-terminating signal to the light controlling device 46 is connected to the first photodector 34 through the second photodetector 48 and the signal line 36.

Figure 2:
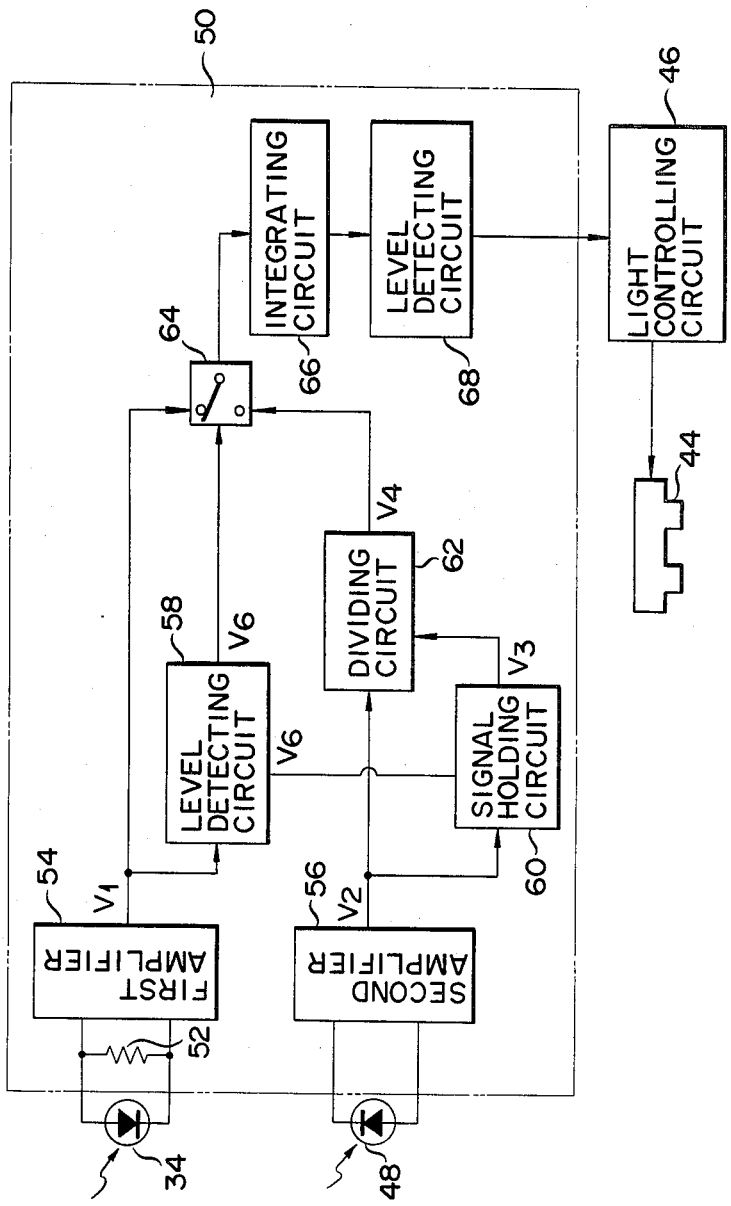
FIG. 2 is a block diagram of the light measuring circuit shown in FIG. 1.

The light measuring circuit 50 is constructed as shown in FIG. 2. The first photodetector 34 which is, for example, a photodiode, is connected in parallel to a resistor 52 for adjusting the sensitivity of this photodiode. To this first photodiode 34 is also connected a first amplifier 54 for amplifying a first luminance signal supplied by the first photodiode 34 which corresponds with the luminance of the to-be-examined region 26. To the second photodetector 48, for example, a photodiode, is connected a second amplifier 56 for amplifying a second luminance signal supplied by the second photodiode which corresponds with the luminance of the flash lamp 44. To the first amplifier 54 is connected a voltage level detecting circuit 58 for generating a saturation signal v6 when the first luminance signal v1 from the amplifier 54 has reached a saturation voltage Vs of the first photodiode 34. The second amplifier 56 is connected to a signal holding circuit 60 which holds the second luminance signal v2 supplied from the second amplifier 56 and amplifies it with an amplification k when it has received the saturation signal v6 from the voltage level detecting circuit 58. This amplification k is selected to be the inverse of the saturated signal Vs obtained by amplifying the voltage of the resistor 52 at the amplifier 54 when the photodetector 34 is saturated, that is, k=(1/Vs). The second amplifier 56 and the signal holding circuit 60 are connected to a dividing circuit 62 which divides the second luminance signal v2 supplied from the second amplifier 56 by a correction signal v3=kv2 to obtain a corrected luminance signal v4. An analog switch 64 provides first and second contacts respectively connected to the first amplifier 54 and the dividing circuit 62, and the fixed contact is switched from the first contact to the second contact when the voltage level detecting circuit 58 has detected the saturation signal v6. An integrating circuit 66 for integrating the luminance signal is connected to the fixed contact of the analog switch 64. To the integrating circuit 66 is connected a signal level detecting circuit 68 which compares the integrated luminance signal generated from the integrating circuit 66 with a reference signal for properly exposing the film 36 and which generates a flash-terminating signal when the integrated luminance signal has reached the reference signal level. To this signal level detecting circuit 68 is connected the light controlling circuit 46 which energizes the electric flash lamp 44 in response to a synchronous signal and which deenergizes it in response to a flash-terminating signal.

A description will now be made on the relation between the first luminance signal v1 corresponding to the object luminance, detected by the first photodetector 34 and amplified by the first amplifier 54, and the second luminance signal corresponding to the luminance of the light source detected by the second photodetector 48 and amplified by the second amplified 56.

Figure 3A:
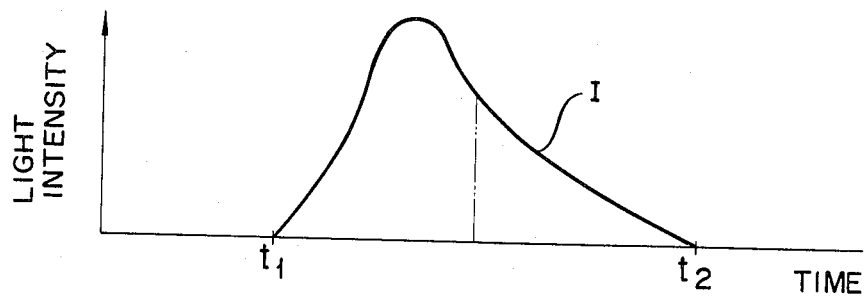
FIG. 3A is a waveform showing the intensity of the light projected from the light guide as a function of the time.

FIG. 3A shows the intensity of the light emitted from the light projecting end face of the image guide 28 and reflected back by the object, that is, the time characteristics of the illuminance of the film surface. Curve I of the intensity of the light reflected from the object is similar to a curve (not shown) of the intensity of the flashlight from the electric flash lamp 44 and is obtained by multiplying the curve of the intensity of the flashlight by an attenuation coefficient to account for transmission losses in the light and image guides and the light reflectivity within the body cavity. The characteristics form a mountain-like curve I in which the peak of the intensity of the light is shifted toward a time t1 and which abruptly increases at the time t1 for starting the flashing of the electric flash lamp 44. The intensity slowly diminishes at a time t2 for terminating the flashing of the electric flash lamp 44.

Figure 3B:
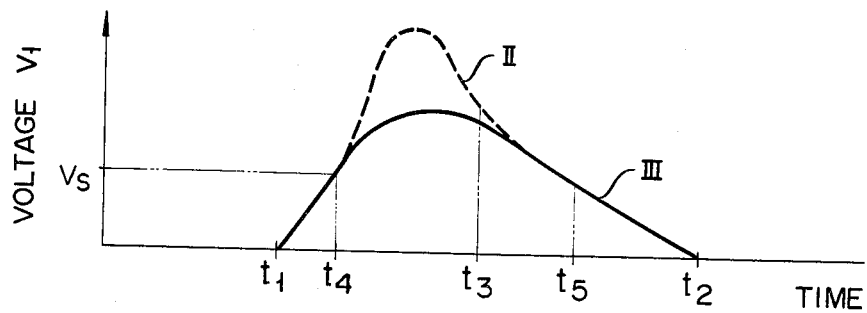
FIG. 3B shows the waveform of the first luminance signal generated by the first amplifier.

FIG. 3B shows the time characteristics of the first luminance signal v1 supplied from the first amplifier 54. Since the light incident on the photosensitive element 34 is part of the light reflected from the object, the characteristic curve III of the first luminance signal v1 may be assumed to be a curve similar to the curve I as shown by dotted curve II. However, since the resistor 52 for adjusting the sensitivity is connected in parallel with the photosensitive element 34, when the current supplied to this resistor 52 is raised to a predetermined value, the photodiode voltage is maintained at a substantially constant voltage, therefore the output voltage from the resistor 52 is saturated and forms a moderate mountain-like curve as shown by solid curve III with a lower peak value than that of the curve II. In general, since the instantaneous intensity of the light at the flashing peak of the electric flash lamp 44 is great, the photosensitive element 34 is saturated so that the first luminance signal v1 does not correctly reflect the luminance of the object. The voltage value at which the dotted curve II and the solid curve III start deviating from each other is shown by a time t4 which corresponds to the saturation voltage, and the object luminance signal v1 takes the saturation value.

Figure 3C:
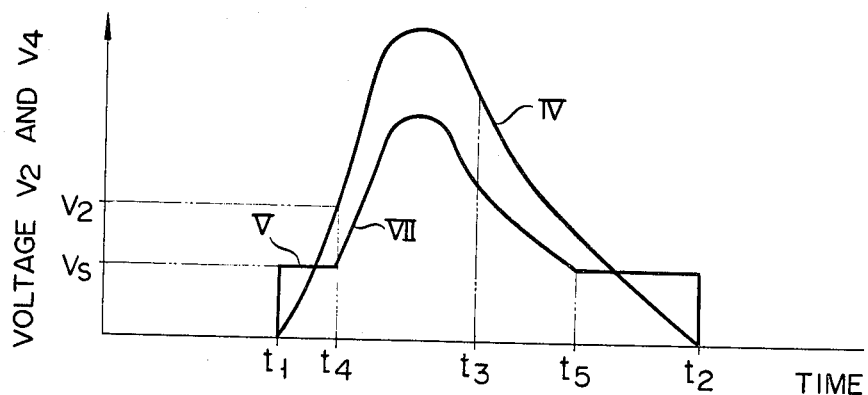
FIG. 3C shows the waveform of the second luminance signal generated by the second amplifier.

FIG. 3C shows the time characteristics of the second luminance signal v2 supplied from the second amplifier 56 in correspondence with the light source luminance. Both ends of the photosensitive element 48 are directly connected to the amplifier 56, and the photo current of the element 48 is amplified by the amplifier 56 to generate the second luminance signal v2. Although the second luminance signal v2 is not adjusted for sensitivity, it shows good response to the intensity of the incident light. Since the light incident on the photosensitive element 48 is part of the flashlight of the electric flash lamp 44, the time characteristics of the second luminance signal v2 form a curve IV similar to the curve I of the intensity of the flash light of the electric flash lamp 44. Since the photodetector 48 is not adjusted for sensitivity by the resistor, this curve IV may become identical with the curve II when multiplied by a certain coefficient.

The mode of operation of the photographing apparatus for an endoscope will now be described with reference to the characteristic curves of FIGS. 3A to 3E.

When the insertion section 12 of the endoscope 2 is inserted into the body cavity and the desired part of the body cavity is within the field of the finder (not shown) of the camera unit 4, a shutter release button (not shown) of the camera unit 4 is depressed to close a synchronous switch (not shown). Then, a closing signal of the synchronous switch is supplied to a trigger circuit (not shown) of the electric flash lamp 44 so that this circuit may initiate the flashing operation of the electric flash lamp 44. The light emitted from the lamp 44 is focused by the condenser lens 42 on the light receiving end face of the light guide 30 and is irradiated on a body cavity 26 from the light projecting end face through the light guide 30. An image of the body cavity 26 is finally formed on the light receiving end face of the image guide 28 by the objective lens 20. Thus, the light of the object reflected by the body cavity inner wall 26 is transmitted through the image guide 28 from the light projecting end face of the image guide 28.

The light from the object transmitted from the light projecting end face of the image guide 28 becomes incident on the photographic film 36 through the beam splitter 32 and the eyepiece lens 24 to expose the film. Part of this light is reflected by the beam splitter 32 and is irradiated on the first photosensitive element 34. A photocurrent is generated in the photodetector 34 and a voltage is induced across the two ends of the resistor 52 for adjusting the sensitivity. Thus, the first amplifier 54 amplifies this voltage and outputs the first luminance signal v1 corresponding to the object luminance.

Part of the light emitted from the electric flash lamp 44 becomes incident on the second photodetector 48. A photocurrent is also generated in the second photosensitive element 48 and is amplified by the second amplifier 56, and the second luminance signal v2 corresponding to the light source luminance is output.

Since the voltage level detection circuit 58 does not generate the saturation signal Vs from the time t1 at which the flashing of the electric flash lamp 44 is initiated to the time t4 at which the first luminance signal v1 reaches the saturation value Vs, the analog switch 64 outputs the first luminance signal v1 to the integrating circuit 66. In this case, the signal holding circuit 60 outputs the signal v3=kv2 obtained by multiplying the second luminance signal v2 by k. Thus, the dividing circuit 62 divides the second luminance signal v2 by the amplified signal v3 and generates from its output terminal a corrected or divided signal v4 shown by a line V in FIG. 3C. The signal v4 is a constant voltage coinciding with the saturation value Vs between times t1 and t4 as may be apparent from the following equation:

$$v4=(v2/v3)=(v2/Kv2)=(1/K)=Vs$$

Figure 3D:
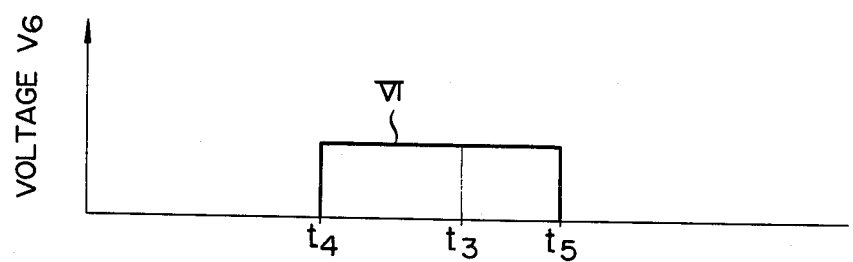
FIG. 3D shows the waveform of the saturated level signal generated by the level detecting circuit.

When the second luminance signal v1 reaches the saturation value Vs, the voltage level detection circuit 58 detects this and outputs the saturation singnal v6 of a constant level shown by line VI in FIG. 3D. In response to this saturation signal v6, the analog switch 64 is switched, and the signal holding circuit 60 holds a value V2 of the second luminance signal v2 at the time t4 and outputs the correction signal v3=kV2 obtained by amplifying the signal v2 by k.

A quotient v4

$$v4=(v2/v3)=(v2/kV2)=Vs/V2)\cdot v2$$

is output at the output terminal of the dividing circuit 62. This signal v4 is the signal obtained by multiplying the light source luminance signal v2 by a certain coefficient. Since the value v4 at the time t4 is $$v4(t4)=(Vs/V2)V2=Vs$$

that is, since it is the same as the saturation value Vs of the photosensitive element 34, its time characteristics form a mountain-like curve VII as shown in FIG. 3C. This curve VII substantially matches the dotted curve II which is obtained when saturation of the photosensitive element 34 does not occur. The quotient signal v4 is output as the luminance signal v4 to the integrating circuit 66 through the analog switch 64 switched in response to the saturation level signal v6 during the period of t4 to t5 in which the first luminance signal v1 exceeds the saturation value Vs.

When the first luminance signal v1 corresponding to the luminance of the object becomes lower than the saturation valve Vs, the voltage level detecting circuit 58 no longer outputs the saturation signal v6 as shown in FIG. 3D after the time t5, and the analog switch 64 is switched so that the first luminance signal v1 is output to the integrating circuit 66. On the other hand, the signal holding circuit 60 releases the holding of the signal value V2, and the dividing circuit 62 outputs the quotient signal v4 of a constant voltage corresponding to the saturation value Vs as shown by the line VIII in FIG. 3C.

Figure 3E:
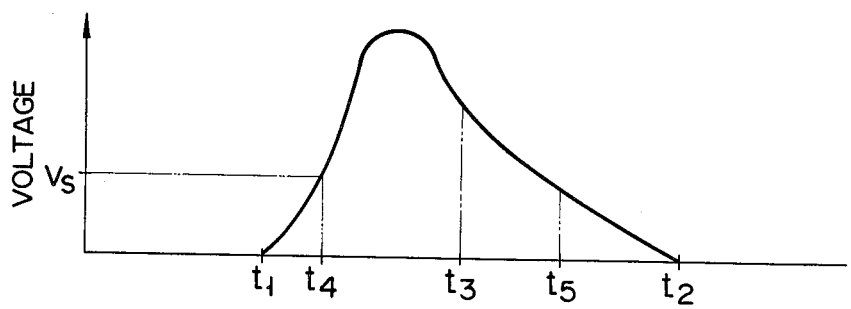
FIG. 3E shows the waveform of the signal supplied to the integrating circuit.

As may be apparent from the above description, in the period of time t1 to t4 and the period of time t5 to time t2 as shown in FIG. 3E, the first luminance signal v1 is supplied from the analog switch 64 to the integrating circuit 66. In the period of t4 to t5, the corrected luminance signal v4 is supplied. Consequently, the integrating circuit 66 integrates the luminance signal proportional to the illuminance of the film surface as shown in FIG. 3A. When the value integrated by this integrating circuit reaches a predetermined level, the flash-terminating signal is output from the level signal detecting circuit 68 and the light controlling circuit 46 deenergizes the electric flash lamp. Accordingly, high precision exposure control may be accomplished according to which the intensity of the light incident on the film surface is correctly calculated.

The alternate long and two short dashed lines in FIGS. 3A to 3E show an example at the time t3 in which the exposure of the photographic film 36 becomes optimal and the flashing of the electric flash lamp 44 is terminated.

According to the photographing apparatus for an endoscope of the present invention, the output of the dividing circuit 62 during the period between the time t1 and t4 and the period between the time t5 and t2 in which the object luminance signal v1 is less than the saturation value Vs does not play any role, so that the operation precision of the output of the dividing circuit 62 may not present any problem during these periods. Thus, it suffices to ensure that the dividing circuit 62 operates correctly only when the object luminance signal v1 exceeds the saturation value Vs.

Figure 4:
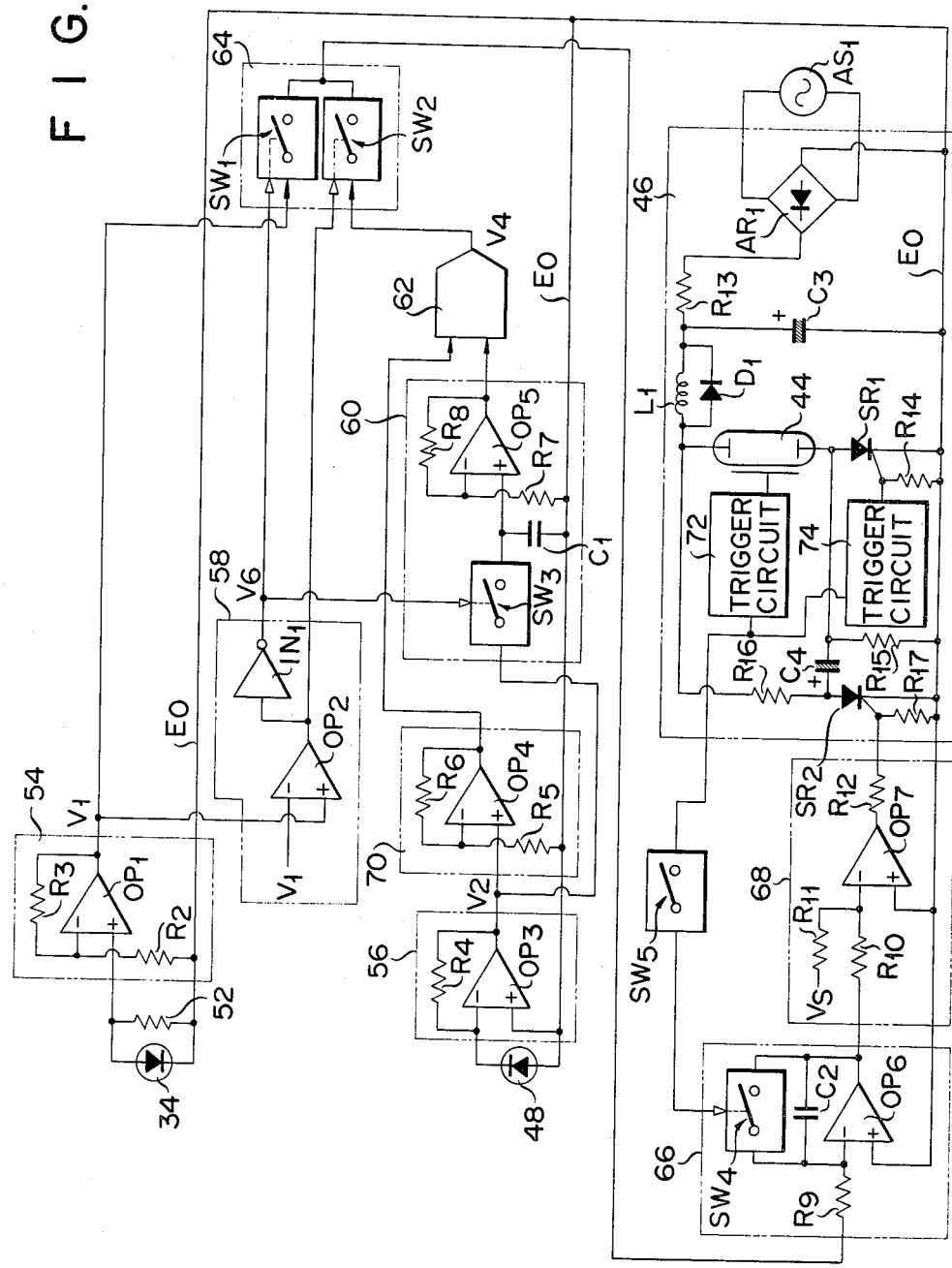
FIG. 4 is a detailed circuit diagram illustrating an example of the circuit of FIG. 2.

FIG. 4 shows an example of the light measuring circuit 50 shown in FIG. 2.

In this circuit, the first amplifier 54 comprises a noninverting amplifying circuit consisting of an operational amplifier OP1 and resistors R2 and R3. In the operational amplifier OP1, the noniverting input terminal is connected to the anode of the photosensitive element 34, and its inverting input terminal is connected to a common earth line E0 through a resistor R2 as well as to its output terminal through a resistor R3.

The voltage level detecting circuit 58 comprises a converter comprising an operational amplifier OP2 and an inverter IN1. In the operational amplifier OP2, the noninverting input terminal is connected to the output terminal of the operational amplifier OP1, and the inverting input terminal is connected to a constant voltage source (not shown) for outputting a constant saturation voltage V1. The output terminal of the operational amplifier OP2 is connected to the control terminal of the other switch SW2 of the analog switch 64 to be described later as well as to the input terminal of the inverter IN1. The output terminal of the inverter IN1 is connected to the control terminal of one switch SW1 of the analog switch 64 as well as to a control switch SW3 of the signal holding circuit 60 to be described hereinafter.

The second amplifier 56 comprises an operational amplifier OP3 and a resistor R4. The photosensitive element 48 is connected between the inverting input terminal and the noninverting input terminal of the operational amplifier OP3. The noninverting input terminal is connected to the common earth line E0. The resistor R4 is connected between the inverting input terminal and the output terminal of the operational amplifier OP3. The output terminal of the operational amplifier OP3 is connected to input terminals of a gain converting circuit 70 and the signal holding circuit 60 of the next stage.

The gain converting circuit 70 is not included in the block diagram shown in FIG. 2. It is a circuit for adjusting the gain of the second luminance signal v2 output from the second amplifier 56 in correspondence with the light source luminance. This gain converting circuit 70 comprises a noninverting amplifying circuit which in turn consists of an operational amplifier OP4 and resistors R5 and R6. The noninverting input terminal of operational amplifier OP4 is connected to the output terminal of the operational amplifier OP3, and the inverting input terminal of the operational amplifier OP4 is connected to the common earth line E0 through the resistor R5 as well as to its output terminal through the resistor R6. The output terminal of the operational amplifier OP4 is connected to one input terminal of the dividing circuit 62.

The signal holding circuit 60 comprises the analog switch SW3, a memory capacitor C1, an operational amplifier OP5, and resistors R7 and R8. In the analog switch SW3, its input terminal is connected to the output terminal of the operational amplifier OP3, its control terminal is connected to the output terminal of the inverter IN1, and its output terminal is connected to the line E0 through the memory capacitor C1 as well as to the noninverting input terminal of the operational amplifier OP5. The inverting input terminal of the operational amplifier OP5 is connected to the line E0 through the resistor R7 as well as to its output terminal through the resistor R8. The output terminal of the operational amplifier OP5 is connected to the other input terminal of the dividing circuit 62.

The amplification k1 of the gain converting circuit 70 is given by the following equation:

$$k1 = (R5 + R6)/R5$$

and the amplification k2 of the signal holding circuit 60 is given by the following equation:

$$k2 = (R7 + R8)/R7$$

where R5 to R8 signify the resistances of the resistors R5 to R8. The resistances of the resistors R5 to R8 are so determined that the signal supplied to one input terminal of the dividing circuit 62 and the signal supplied to the other input terminal have a gain difference of k times. That is, the resistances of the resistors R5 to R8 are determined so as to satisfy the following equation:

$$k = \frac{k2}{k1} = \frac{(R7 + R8)/R7}{(R5 + R6)/R5} = \frac{1}{Vs}$$

The dividing circuit 62 is formed with an integrated circuit used exclusively for division. The signal supplied to one input terminal becomes a numerator and the signal supplied to the other input terminal becomes a denominator to output a quotient signal at the output terminal.

The analog switch 64 comprises two switches SW1 and SW2 which are rendered conductive upon application of a control signal of high level. In the one switch SW1, the input terminal is connected to the output terminal of the operational amplifier OP1, and the control terminal is connected to the output terminal of the inverter IN1. In the other switch SW2, the input terminal is connected to the output terminal of the dividing circuit 62, and the control terminal is connected to the output terminal of the operational amplifier OP2. The outputs of the switches SW1 and SW2 are commonly connected to the input terminal of the integrating circuit 66 of the next stage.

The integrating circuit 66 comprises an operational amplifier OP6, an integrating capacitor C2, an analog switch SW4 for resetting the integrating circuit, and a resistor R9. The inverting input terminal of the operational amplifier OP6 is connected to the output terminal of the analog switch 64 through the resistor R9, and the noninverting input terminal is connected to the common earth line E0. The integrating capacitor C2 and the analog switch SW4 are connected in parallel between the inverting input terminal and the output terminal of the operational amplifier OP6. In the analog switch SW4, its control terminal is connected to a synchroswitch SW5 disposed inside the camera unit 4 so that it is rendered nonconductive in response to a closing signal of the synchroswitch SW5 to make the integrating circuit consisting of the operational amplifier OP6 and the capacitor C2 start integration.

The signal level detecting circuit 68 comprises a converter circuit consisting of an operational amplifier OP7 and resistors R10 to R12. The inverting input terminal of the operational amplifier OP7 is connected to the output terminal of the operational amplifier OP6 through the resistor R10 as well as to a constant voltage source (not shown) through the resistor R11 for outputting a constant reference voltage Vs. The noninverting input terminal of the operational amplifier OP7 is connected to the common earth line E0, and its output terminal is connected through the resistor R12 to the gate of a thyristor SR2 for interrupting emission of light of the light controlling circuit 46 to be described later. The reference voltage Vs may be varied according to the sensitivity of the photographic film 36.

The light controlling circuit 46 comprises a known light controlling circuit of the electronic flash series control type. The light controlling circuit 46 comprises a full-wave rectifying circuit AR1 connected to an AC power source AS1, a main capacitor C3, a main thyristor SR1 as a main switching element, an electric flash lamp trigger circuit 72, a main thyristor trigger circuit 74, a commutating capacitor C4, the thyristor SR2 as a light-interrupting trigger circuit, a current-limiting coil L1, a surge voltage absorbing diode D1, and resistors R13 to R17.

The full-wave rectifying circuit AR1 comprises a known single phase full-wave rectifying circuit formed by connecting four rectifying diodes in a bridge. The plus terminal of the full-wave rectifying circuit AR1 is connected to one terminal of the main capacitor C3 through the resistor R13, and the minus terminal is connected to the common earth line E0. The other terminal of the main capacitor C3 is connected to the common earth line E0. A series circuit of a parallel connection of the coil L1 and the diode D1, the electric flash lamp 44, and the main thyristor SR1 is connected in parallel with the main capacitor C3. The trigger electrode of the electric flash lamp 44 is connected to the electric flash lamp trigger circuit 72 which is connected to the synchroswitch SW5 of the camera unit 4. In response to a closing signal of the synchroswitch SW5, the trigger circuit 72 is operated to apply a high voltage to the trigger electrode of the electric flash lamp 44.

The anode of the main thyristor SR1 is connected to the cathode electrode of the electric flash lamp 44, the cathode of the main thyristor SR1 is connected to the line E0, and its gate is connected to the line E0 through the resistor R14 as well as to the main trigger circuit 74. The main thyristor trigger circuit 74 is connected to the synchroswitch SW5 of the camera unit 4. In response to a closing signal of the synchroswitch SW5, the trigger circuit 74 is operated to trigger the gate of the thyristor SR1 and to fire the thyristor SR1. Since the trigger circuits 72 and 74 are of known type, the detailed description thereof will be omitted.

With the series connection of the electric flash lamp 44 and the main thyristor SR1 is connected in parallel a series circuit of the resistor R16 and the light interrupting thyristor SR2. The cathode of the thyristor SR2 is connected to the common earth line E0, and its gate is connected to the line E0 through the resistor R17 as well as to the output terminal of the signal level detecting circuit 68. A series circuit of the commutating capacitor C4 and the resistor R15 is connected in parallel with the thyristor SR2. The node of the capacitor C4 and the resistor R15 is connected to the anode of the main thyristor SR1.

The light controlling circuit 46 is of the construction described above. The mode of operation of this circuit will now be simply described together with the mode of operation of the photographing apparatus for an endoscope.

When the shutter release button (not shown) disposed in the camera unit 4 is depressed to close the synchroswitch SW5, the closing signal of this switch is supplied to the trigger circuits 72 and 74. Then, a high voltage is applied to the trigger electrode of the electric flash lamp 44 and the main thyristor SR1 is fired to start the flashing operation of the electric flash lamp 44. Simultaneously with this, the closing signal of the synchroswitch SW5 is supplied to the analog switch SW4 to render the switch SW4 nonconductive and to start the integrating operation of the integrating circuit 66.

The light emitted by the electric flash lamp 44 is guided by the light guide 30 of the endoscope 2 to the inside of the body cavity. The object light reflected back from the body cavity inner wall 26 becomes incident on the camera unit 4 through the image guide 28. Part of the object light is also incident on the photosensitive element 34. The light incident on the photosensitive element 34 generates a photocurrent in the element 34 which in turn induces a voltage across the ends of the sensitivity adjusting resistor 52. This voltage is amplified by the first amplifier 54 $(R2+R3)/R2$ times, and the amplified voltage is then output as the first luminance signal v1 corresponding to the object luminance. The first luminance signal v1 is input for integration in the integrating circuit 66 through the switch SW1 of the analog switch 64.

Part of the light emitted from the electric flash lamp 44 is received by the photosensitive element 34 which generates a photocurrent corresponding to the intensity of the incident light. The photocurrent is amplified and is output as the second luminance signal v2 corresponding to the light source luminance.

When the luminance of the light emitted by the electric flash lamp 44 gradually increases from the time t1 for starting the emission of the light, the object luminance signal v1 reaches a saturation voltage value Vs. Then, the output of the operational amplifier OP2 of the signal level detecting circuit 68 changes to a voltage of high level. As a result, the output of the inverter IN1 becomes one of low level to render the switch SW1 of the analog switch 64 nonconductive and to render the other switch SW2 conductive by the output of high level of the operational amplifier OP2, so that the analog switch 64 is switched. Simultaneously with this, the output of low level of the inverter IN1 renders the analog switch SW3 of the signal holding circuit 60 nonconductive so that the voltage value V2 of the second luminance signal v2 at the time t4 is held by the memory capacitor C1. The light source luminance signal v2 at the time t4 is amplified (R7+R8)/R7 times by the amplifying circuit of the operational amplifier OP5 and is input to the other input terminal of the dividing circuit 62.

The light source luminance signal v2 output from the amplifying circuit 56 is amplified (R5+R6)/R5 times by the gain converting circuit 70 and is input to one input terminal of the dividing circuit 62. Therefore, the dividing circuit 62 outputs a signal represented by the following equation:

$$v4 = \frac{(R5 + R6)/R5 \cdot V2}{(R7 + R8)/R7 \cdot V2} = \frac{V1}{V2} v2$$

The output of the dividing circuit 62 is input to the integrating circuit 66 through the other switch SW2 of the analog switch 64 as the object luminance signal v4 for correction. Although the signal input to the integrating circuit 66 changes from the first luminance signal v1 to the second luminance signal v4, the integrating circuit 66 continues to integrate the object luminance signal v4 for correction.

When the photographic film 36 is exposed to the optimal amount of light and the integrated voltage at the integrating circuit 66 becomes less than −Vs, the inverting input terminal of the operational amplifier OP7 of the level detection circuit 68 becomes negative, and the output of the operational amplifier OP7 changes from low level to high level. Thus, the gate of the thyristor SR2 for interrupting emission of the light of the light controlling circuit 46 is triggered to fire the thyristor SR2 to conduct it. Thus, the ends of the commutating capacitor C4 are short-circuited through the thyristor SR2 and the resistor R15 so that the anode of the main thyristor SR1 is biased negatively and the main thyristor SR1 is rendered nonconductive. The flashing of the electric flash lamp 44 is then interrupted, and exposure of the photographic film 36 to light is terminated.

Although the photosensitive element 34 as the means for measuring the object light was disposed at the eyepiece part 10 of the endoscope 2 in the above embodiment, it may alternatively be disposed within the camera unit 4.

Although the dividing circuit 62 was constantly operated in the above embodiment, it may be operated only when the saturation signal v6 is supplied to the dividing circuit 62 by so arranging the circuit.

What is claimed is:

1. A photographing apparatus for an endoscope comprising:
   an endoscope having a light guide for transmitting light to a region to be photographed, and an image guide for transmitting light reflected from the region to be photographed;
   a flash light source for emitting light for photographing into the light guide of said endoscope;
   a camera unit for housing a film to which is projected a light beam transmitted through the image guide of said endoscope, said camera unit having shutter means disposed in the optical path of the light beam for opening and closing the optical path of the light beam, and further having means for generating a synchronous signal for opening the shutter means;
   a first photoelectric converter for detecting part of the light beam transmitted through said light guide;
   a resistor connected in parallel with said first photoelectric converter;
   a first amplifier coupled to said resistor for amplifying a voltage generated across said resistor;
   means coupled to said first amplifier for generating a switching signal when a first voltage signal amplified by said first amplifier has reached a predetermined level;
   a second photoelectric converter for detecting part of the flash of light generated by said flash light source, and across which no resistor is coupled;
   a second amplifier coupled to said second photoelectric converter for amplifying a voltage generated by said second photoelectric converter;
   correction signal generating means coupled to said second amplifier for holding the level of a second voltage signal amplified by said second amplifier in response to said switching signal and for generating a correction signal obtained by amplifying the second voltage signal of said level by a constant factor;
   means coupled to said second amplifier and to said correction signal generating means for generating a divided signal obtained by dividing said second voltage signal generated by said second amplifier by said correction signal;
   integrating means for integrating a supplied signal;
   switching means for switching the signal supplied to said integrating means from said first voltage signal to said divided signal in response to said switching signal;
   means coupled to said integrating means for generating a flash-terminating signal when the output from said integrating means reaches a predetermined level; and
   means for energizing said flash light source in response to a synchronous signal and for deenergizing said flash light source in response to said flash-terminating signal.

2. An apparatus according to claim 1, wherein said switching signal generating means generates a switching signal when the first voltage generated by said first amplifier reaches a saturation level or a predetermined level lower than the saturation level.

3. An apparatus according to claim 1, wherein said switching signal generating means generates a first switching signal when the first voltage signal generated by said first amplifier increases to a predetermined level and generates a second switching signal when the first voltage signal decreases to a predetermined level; and said switching means switches a signal supplied to said integrating means from the first voltage signal to a divided signal in response to the first switching signal, and switches the signal supplied to the integrating means from the divided signal to the first voltage signal in response to the second switching signal.

4. An apparatus according to claim 1, wherein said correction signal generating means amplifies a held second voltage signal by a constant factor which is the inverse of the signal level at which said switching signal generating means generates a switching signal.

5. An apparatus according to claim 4, wherein said signal level is a level at which the first voltage signal is saturated.

* * * * *